United States Patent
Versalovic et al.

(10) Patent No.: US 10,898,529 B2
(45) Date of Patent: *Jan. 26, 2021

(54) PRODUCTION AND USE OF BACTERIAL HISTAMINE

(71) Applicant: BioGaia AB, Stockholm (SE)

(72) Inventors: James Versalovic, Bellaire, TX (US); Carissa Michelle Thomas, Houston, TX (US); Eamonn Connolly, Lindingo (SE)

(73) Assignee: BIOGAIA AB, Stockholm (SE)

( * ) Notice: Subject to any disclaimer, the term of this patent is extended or adjusted under 35 U.S.C. 154(b) by 202 days.

This patent is subject to a terminal disclaimer.

(21) Appl. No.: 15/987,210

(22) Filed: May 23, 2018

(65) Prior Publication Data

US 2018/0264055 A1 Sep. 20, 2018

Related U.S. Application Data

(62) Division of application No. 15/289,666, filed on Oct. 10, 2016, now Pat. No. 10,004,770, which is a division of application No. 13/552,686, filed on Jul. 19, 2012, now abandoned.

(60) Provisional application No. 61/572,742, filed on Jul. 21, 2011.

(51) Int. Cl.
```
A61K 35/747    (2015.01)
A23L 33/135    (2016.01)
C12Q 1/04      (2006.01)
A61K 35/741    (2015.01)
G01N 33/569    (2006.01)
A61K 31/4172   (2006.01)
A61K 35/74     (2015.01)
A23L 33/175    (2016.01)
A61K 31/7004   (2006.01)
A61K 45/06     (2006.01)
A61K 35/00     (2006.01)
```

(52) U.S. Cl.
CPC .......... *A61K 35/747* (2013.01); *A23L 33/135* (2016.08); *A23L 33/175* (2016.08); *A61K 31/4172* (2013.01); *A61K 31/7004* (2013.01); *A61K 35/74* (2013.01); *A61K 35/741* (2013.01); *A61K 45/06* (2013.01); *C12Q 1/04* (2013.01); *G01N 33/56911* (2013.01); *A23V 2002/00* (2013.01); *A23Y 2220/71* (2013.01); *A61K 2035/115* (2013.01); *G01N 2333/335* (2013.01)

(58) Field of Classification Search
CPC .............................. A61K 35/74; A61K 35/744
See application file for complete search history.

(56) References Cited

U.S. PATENT DOCUMENTS

| | | | |
|---|---|---|---|
| 7,344,867 B2 * | 3/2008 | Connolly | A61K 38/164 424/93.45 |
| RE40,457 E * | 8/2008 | Cavaliere ved. Vesely | A23C 9/1234 424/93.3 |
| 10,004,770 B2 * | 6/2018 | Versalovic | A61P 1/02 |
| 2008/0254011 A1 | 10/2008 | Rothschild et al. | |
| 2013/0022586 A1 | 1/2013 | Versalovic et al. | |
| 2013/0149291 A1 | 6/2013 | Versalovic et al. | |

FOREIGN PATENT DOCUMENTS

| | | |
|---|---|---|
| ES | 23106 | 12/2008 |
| WO | 2006/110088 | 10/2005 |
| WO | 2010/013143 | 2/2010 |
| WO | 2010/027344 | 3/2010 |

OTHER PUBLICATIONS

Williamson M.B. "The amino acid composition of human milk proteins". J Biol Chem., 1944, 156, pp. 47-52.*
Calles-Enriuzez, M. et al., "Sequencing and Transcriptional Analysis of *Streptococcus thermophiles* Histamine Biosynthesis Gene Cluster: Factors that Affect Differential hdcA Expression", Appl. Environ. Microbial. 76:6231-38, 2010.
Casas, I.A. et al., "Validation of the Probiotic Concept: Lactobacillus reuteri Confers Broad-spectrum Protection against Disease in Humans and Animals", Microbial Ecology in Health and Disease, (2000), 45 pages.
De Las Rivas, B. et al., Improved muitiplex-PCR method for simultaneous detection of food bacteria producing biogenic amines, FEMS Microbial, Ltrs. 244:367-72, 2005.
Histamine Toxicity Symptoms: Diagnosis, Treatment and Management, American Academy of Allergy Asthma & Immunology at http://www.aaaai.org/conditions-and-treatments/related-conditions/histamine-toxicity (2017).
Ladero, V. et al., "Biogenic amines content in Spanish and French natural ciders: Application of qPCR for quantitative detection of biogenic amine-producers", Food Microbiol, 28:554-61, 2011.
Liu, Y. et al., "Human-deprived Probiotic Lactobacillus reuteri strains differentially reduce intestinal inflammation", Am. J. Physiol. Gastrointest Liver Physiol. 299:G1087-96, 2010.
Lucas, P.M., et al., "Histamine-producing Pathway Encoded on an Unstable Plasmid in Lactobacillis hilgardii 0006", Appl. Environ. Microbiol. 71:1417-24, 2005.

(Continued)

*Primary Examiner* — Vera Afremova
(74) *Attorney, Agent, or Firm* — Myers Bigel, P.A.

(57) ABSTRACT

A method is provided of selecting specific probiotic lactic acid bacteria producing histamine and the use of such strains for beneficial effects for mammals. The method includes selecting a lactic acid bacterial strain for use in the local production of histamine in a mammal, and further comprises screening bacteria for the presence of an active histidine operon and selecting a strain which has an active histidine operon and is capable of producing histamine. Preferably said strain is selected for its ability to produce histamine at a level of greater than 250 pg/ml. The present invention further provides products comprising the strains obtainable by the selection methods of the invention for use in the local production of histamine in a mammal, in particular for use in the treatment or prophylaxis of inflammatory conditions.

10 Claims, 7 Drawing Sheets

(56) References Cited

OTHER PUBLICATIONS

Nikawa et al., "Lactobacillus reuteri in bovine milk fermented decreases the oral carriage of mutans streptococci", International Journal of Food Microbiology 95:219-223, 2004.
Straub, B.W. et al., "The formation of biogenic amines by fermentation organisms", Z. Lebensm Imters Forsch 201:79-82, 1995.
Sumner, S. et al., "Isolation of Histamine-production Lactobacillis Buchneri from Swiss Cheese Implicated in a Food Poisoning Outbreak", Appl. Environ. Micro. 50:1094-96, 1985.
Thomas, C.M. et al., "Histamine Derived from Probiotic Lactobacillus reuteri Suppresses TNF via Modulation of PKA and ERK Signaling". PLOS ONE 7:1-15, 2012.
Trip, H. et al., HdcB, a novel enzyme catalyzing maturation of pyruvoyl-dependent histidine decarboxylase, Molecular Microbiol, 79:861-71, 2011.
Vannier, E. et al., Histamine Suppresses Gene Expression and Synthesis of Tumor Necrosis Factor Alpha via Histamine H2 Receptors, J. Exp. Med. 174:281-84, 1991.
Wang, J. et al., "Histamine Antagaonizes Tumor Necrosis Factor (TNF) Signaling by Stimulating TNF Receptor Shedding from the Cell Surface and Golgi Storage Pool", J. Biol. Chem. 278:21751-760, 2003.

\* cited by examiner

PRODUCTION AND USE OF BACTERIAL HISTAMINE

CROSS-REFERENCE TO RELATED APPLICATIONS

This application is a divisional application of U.S. patent application Ser. No. 13/552,686 filed on Jul. 19, 2012, which claims the benefit, under 35 U.S.C. § 119 (a), of U.S. Provisional Application No. 61/572,742 filed Jul. 21, 2011.

FIELD OF THE INVENTION

This invention relates to a method of selecting specific probiotic lactic acid bacteria producing histamine and the use of such strains to deliver beneficial effects for the host.

BACKGROUND OF THE INVENTION

The Food and Agricultural Organization of the United Nations define probiotics as "live microorganisms which when administered in adequate amounts confer a health benefit on the host". Nowadays, a number of different bacteria are used as probiotics for example, lactic-acid producing bacteria such as strains of *Lactobacillus* and *Bifidobacteria*.

Lactic-acid producing bacteria are not only used for their beneficial effect on human or animal health, but they are also widely used in the food industry for fermentation processes. The effectiveness of probiotics is strain-specific, and each strain may contribute to host health through different mechanisms. Probiotics can prevent or inhibit the proliferation of pathogens, suppress production of virulence factors by pathogens, or modulate the immune response in a pro-inflammatory or an anti-inflammatory way. Use of different strains of the probiotic lactic-acid producing bacteria *Lactobacillus reuteri* is a promising therapy for the amelioration of infantile colic, alleviation of eczema, reduction of episodes of workplace illness, and suppression of *Helicobacter pylori* infection. *L. reuteri* is considered an indigenous organism of the human gastrointestinal tract and is present for example on the mucosa of the gastric corpus, gastric antrum, duodenum, and ileum. See, for example, U.S. Pat. Nos. 5,439,678, 5,458,875, 5,534,253, 5,837,238, and 5,849,289.

When *L. reuteri* cells are grown under anaerobic conditions in the presence of glycerol, they produce the antimicrobial substance known as reuterin (β-hydroxy propionaldehyde).

The relationship between a host and its microbes is complex, and for some bacteria, this host: microbe relationship has been developing over many years of co-evolution. This appears to be especially true for *Lactobacillus reuteri*. Our knowledge of the mutualistic relationship between gut microbes and the human host is in its infancy, but already we are keenly aware that the gut microbiome plays an essential role in gut and immune system development, nutrition, and new links are being established between the gut microbiome and the brain. Dysbiosis, the perturbation of the normal gut microbiome, has been implicated in a wide range of disease processes including those affecting the local gut environment, such as Inflammatory Bowel Disease (IBD) and Irritable Bowel Syndrome (IBS), and disease processes at sites distant to the gut, such as the metabolic syndrome. Significant therapeutic potential lies within the gut microbiome, and research is striving towards a future goal of altering the microbial community in order to prevent and/or treat distinct disease processes.

There is therefore a need to understand such specific interactions between microbes and man related to a specific disease or other situations influencing the health of the host so that the most appropriate probiotic strains can be selected and used to counteract such developments.

SUMMARY OF THE INVENTION

The invention herein provides a specific method of locally producing histamine in mammals, especially humans, the local production of histamine includes but are not limited to production in the GI tract, genitourinary (GU) tract, oral cavity, in the lungs and airways, on the skin etc, of the mammalian body by selecting certain strains of lactic acid bacteria. The bacteria may be delivered together with certain amino acids and/or sugars, separately administered or already present at the active site.

A primary object of the present invention is to select strains that can locally produce histamine in various locations, including the GI tract. GU tract, oral cavity, in the lungs and airways, on the skin etc, of the mammalian body.

It is a further object of the invention to provide products containing said strains.

It is a further object of the invention to combine the administration of bacteria with administration of histidine, or histidine-containing foods or compositions, to ensure local generation of histamine.

The present invention thus relates to a new method for selecting lactic acid bacterial cells which are useful as probiotics and in therapy. This new method involves the screening and selection for strains of lactic acid bacteria which have an active histidine operon and are capable of producing histamine. Surprisingly, the lactic acid bacterial strains selected by this method are useful as probiotics and in therapy, in particular in producing anti-inflammatory effects, by way of the local production of histamine. These effects of the bacteria are surprising, as discussed elsewhere herein, previously the presence in foodstuffs of bacteria producing histamine was actively avoided due to the recognized health risk, for example potential toxic effects. Thus, the administration to a mammal of lactic acid bacteria capable of local production of histamine, or indeed the screening and selection of lactic acid bacteria for such capability of local production of histamine based on the presence of an active histidine operon and an ability to produce histamine is counter-intuitive to this teaching. Indeed, probiotics have never before been reported to produce histamine.

Thus, at its broadest, the present invention provides a method of selecting a lactic acid bacterial strain for use in the local production of histamine in a mammal, wherein said method comprises screening bacteria for the presence of an active histidine operon and selecting a strain which has an active histidine operon and is capable of producing histamine.

The histidine operon comprises three genes (the histidineistamine antiporter, the histidine decarboxylase pyruvoyl type A (HdcA), and histidine decarboxylase pyruvoyl type B (HdcB)). It is believed that the activity of each of these genes is important for the present invention. Thus, in the screening methods of the invention, candidate bacteria are assessed for the presence of all three genes and strains positive for all three genes are selected. Any appropriate method can be used for the detection of the presence of all three genes, for example genetic methods such as PCR can be used. The production of good levels of histamine can also be an indicator of the presence of all three genes and the presence of an active histidine operon. Thus, the selection method of the invention also involves the step of selecting a strain which is capable of producing histamine. Strains with high production levels of histamine are preferred. Thus, in preferred embodiments a strain is selected for its ability to produce histamine at a level of greater than 200, preferably greater than 250 or more preferably greater than 300 pg/ml, for example a level of greater than 350, 400, 450, or 500 pg/ml. Such values generally refer to values of histamine measured in the supernatant of strains in culture.

Appropriate methods of measuring levels of histamine production would be well known to a person skilled in the art. The method of mass spectrometry, more specifically triple quadrupole mass spectrometry, is exemplified herein and is preferred. However, equally ELISAs or immunoassays can be used to evaluate and quantify histamine production. Thus, in some embodiments of the invention, the selection method will involve the step of detecting the amount or level of histamine produced by a candidate strain. Because of the downstream uses of the strains which are selected by the methods of the invention, after histamine-producing strains are selected or isolated, other embodiments will involve the further steps of culturing or propagating such strains, or possibly storing such strains for future uses.

Such further steps (and indeed the selection steps of the methods of the invention) will generally need to be carried out in an appropriate culture medium which supports histamine production. Preferred culture media will contain an appropriate carbon source which will support the production of histamine by said strain. In particularly preferred embodiments, the media will comprise glucose as a carbon source and preferably will not contain sucrose, or at least will only comprise sucrose at such a level which will not significantly compromise histamine production by the strain. Histidine or a histidine analog can also be provided, optionally together with sources of other amino acids.

In preferred embodiments said strain is a strain of *Lactobacillus reuteri*.

Once an appropriate strain has been selected using the method of the present invention it can then be used for the local production of histamine in a mammal. Said strains thus also have to be capable of local production of histamine in a mammal.

Thus, a further aspect of the present invention provides a product comprising cells of a lactic acid bacterial strain obtainable by the selection method of the invention, wherein said lactic acid bacterial strain has an active histidine operon and is capable of producing histamine, for use in the local production of histamine in a mammal. As will be outlined elsewhere herein, preferred uses are in the treatment and/or prophylaxis of inflammatory conditions, or in the treatment and/or prophylaxis of conditions or diseases which will benefit from local histamine production. For example, such local production of histamine can result in an anti-inflammatory effect.

Alternative embodiments of the invention provide a lactic acid bacterial strain which is capable of producing histamine for use in the local production of histamine in a mammal, wherein said lactic acid bacterial strain has an active histidine operon. Preferred features of this strain and its uses are described elsewhere herein.

Methods of treatment or methods for the local production of histamine in a mammal, are also provided, said methods comprising the administration of a product comprising cells of a lactic acid bacterial strain obtainable by the selection method of the invention, or the administration of a lactic acid bacterial strain wherein said lactic acid bacterial strain has an active histidine operon and is capable of producing histamine, to said mammal in an amount effective to enable local production of histamine in said mammal. Preferred features of the strain and its therapeutic uses are described elsewhere herein.

Also provided by the present invention is the use of a product comprising cells of a lactic acid bacterial strain obtainable by the selection method of the invention, wherein said lactic acid bacterial strain has an active histidine operon and is capable of producing histamine, in the manufacture of a composition or medicament for use in the local production of histamine in a mammal. Alternative embodiments provide the use of a lactic acid bacterial strain, wherein said lactic acid bacterial strain has an active histidine operon and is capable of producing histamine, in the manufacture of a composition or medicament for use in the local production of histamine in a mammal. Preferred features of the strain and its therapeutic uses are described elsewhere herein.

DETAILED DESCRIPTION OF THE INVENTION

The inventors herein have found that a selected group of lactobacilli, including certain strains of *Lactobacillus reuteri* locally produces histamine under specific growth conditions, and that such produced histamine will benefit the host by for example reducing inflammation, reducing certain cancers etc.

Histamine

Histamine is an organic nitrogen compound involved in several health-associated processes of a mammal, including local immune responses as well as regulating physiological function in the gut and acting as a neurotransmitter. As part of an immune response to foreign pathogens, histamine is produced by basophils and mast cells. Histamine can be derived from the decarboxylation of the amino acid histidine, a reaction catalyzed by the enzyme L-histidine decarboxylase.

Bacteria are capable of producing histamine using histidine decarboxylase enzymes unrelated to those found in eukaryotes. Up to now, such production of histamine by certain bacterial strains has been seen as a health risk rather than a possible benefit for humans. For example, Scombroid poisoning, a form of non-infectious foodborne disease, is due to histamine production by bacteria in spoiled food, particularly fish. Fermented foods and beverages naturally contain small quantities of histamine due to a similar conversion performed by fermenting bacteria or yeasts. Delivery of certain controlled amounts of histamine from selected bacteria can, surprisingly, give beneficial effects rather than detrimental effects as might be expected from the above mentioned studies.

Histamine receptors are a class of G protein-coupled receptors with histamine as their endogenous ligand. There are four known histamine receptors; $H_1$receptor (H1R), $H_2$receptor (H2R), $H_3$receptor (H3R) and H4receptor (H4R).

Vannier et al. (*Histamine Suppresses Gene Expression and Synthesis of Tumor Necrosis Factor α via Histamine $H_2$ Receptors*; J Exp Med. 1991 Jul. 1; 174(1):281-4) showed that LPS-induced synthesis of TNF-α in peripheral blood mononuclear cells was suppressed by histamine and they further suggest that histamine release from mast cells may limit the extent of inflammatory and immune reactions by suppressing local cytokine synthesis in $H_2$ receptor-bearing cells.

The anti-inflammatory activity of histamine has previously been disclosed by Wang et al. (*Histamine Antagonizes Tumor Necrosis Factor (INF) Signaling by Stimulating TNF Receptor Shedding from the Cell Surface and Golgi Storage Pool*; J. Biol. Chem. 278(24): 21751-21760), showing that histamine causes transient loss of surface TNFR1, increased TNFR1 shedding, and mobilization of TNFR1 molecules from the Golgi in cultured human endothelial cells. Histamine injection into human skin engrafted on immunodeficient mice caused shedding of TNFR1 and diminished TNF-mediated induction of endothelial adhesion molecules.

Vannier et al. and Wang et al. did not mention anything about using histamine-producing bacterial strains as probiotics nor how to select the strains based on their histamine-producing abilities in order to assure certain health benefits for the host, such as anti-inflammatory effects.

Ceplene, a pharmaceutical-grade form of histamine dihydrochloride, is used for the prevention of relapse in patients diagnosed with acute myeloid leukemia (AML). Ceplene is administered in conjunction with low doses of the immune-activating cytokine interleukin-2 (IL-2) in the post-remission phase of AML, i.e. when patients have completed the initial chemotherapy. Studies have shown that Ceplene/IL-2 can induce immune-mediated killing of leukemic cells. The treatment, subcutaneous injections, is given in 3-week cycles by the patients at home for 18 months. The side effects of Ceplene include transient flush and headache. It would be advantageous for patients to receive locally produced histamine, when needed, instead of subcutaneous injections; this delivery strategy may be achieved by administering bacterial-derived histamine to the patient using the strains selected according to this invention.

It is previously known that gram-negative bacteria form histamine for example in raw fish and meat following temperature abuse and that gram-positive bacteria cause histamine spoilage of fermented foods such as cheese, sausage, miso, soy sauce, beer and wine. The identification of histamine-producing bacteria in foods has been difficult.

Also *Lactobacillus reuteri* has previously been associated with histamine production, Casas et al. (*Validation of the Probiotic Concept: Lactobacillus reuteri Confers Broad-spectrum Protection against Disease in Humans and Animals.;* 2000, ISSN 0891-060X) reports that two strains of *L. reuteri* in the hands of Straub et. al. (Z Lebensm Unters Forsch (1995) 201; 79-82) has been shown to decarboxylate L-histidine to form histamine and the authors warn against using such strains for the fermentation of food and as probiotics.

Trip et al. (*HdcB, a novel enzyme catalyzing maturation of pyruvoyl-dependent histidine decarboxylase*; Molecular Microbiology (2011) 79(4), 861-871) referring to three types of genetic organization of histidine decarboxylation loci among histamine-producing Gram-positive bacteria. The largest group is found in the lactic acid bacteria including *L. hilgardii* 0006. *L. buchneri* B301. *L. reuteri* F275 and *T. halophilus. Lactobacillus hilgardii* 0006 has been shown to produce histamine, in a study performed by Lucas et al. (*Histamine-Producing Pathway Encoded on an Unstable Plasmid in Lactobacillus hilgardii 0006*; APPLIED AND ENVIRONMENTAL MICROBIOLOGY, March 2005, Vol. 71, No. 3, p. 1417-1424), they further say that histamine is a contaminant that appears in several products during growth of undesirable bacteria Lucas et al. have performed a screening of a collection of wine lactic acid bacteria to identify the genes involved in the histamine-producing pathway of a gram-positive bacterium of wine.

A histamine-producing strain of *Lactobacillus buchneri* has been isolated from Swiss cheese that had been implicated in an outbreak of histamine poisoning (Summer et al. *Isolation of histamine-producing Lactobacillus buchneri from Swiss cheese implicated in a food poisoning outbreak*; Applied and Environmental Microbiology (1985), Vol. 50, Issue 4, p. 1094-1096).

Calles-Enríquez et al. (*Sequencing and Transcriptional Analysis of the Streptococcus thermophiles Histamine Biosynthesis Gene Cluster: Factors That Affect Differential*

*hdcA Expression*; APPLIED AND ENVIRONMENTAL MICROBIOLOGY, September 2010, Vol 76, No. 18, p. 6231-6238) describe histamine-producing strains of *Streptococcus thermophiles*, a thermophilic starter used for the production of yogurt and certain cheese varieties. They further indicate that the presence of strains with the capacity to decarboxylate histidine could result in products containing histamine produced during manufacture or during storage before consumption and that this underlies the importance of using only histamine-negative strains in the manufacture of fermented dairy products.

Even if it has been previously known that some *Lactobacillus* can produce histamine it has certainly not been known that the ability to produce histamine is a key factor to assure certain health benefits for it's host, for example anti-inflammatory properties of certain *Lactobacillus* strains.

Neither is it known or obvious from the prior art that this can be used for screening and selection of certain probiotic strains of *Lactobacillus*.

Mast Cells

A mast cell (also known as mastocyte and labrocyte) is a resident cell of several types of tissues and contains many granules rich in histamine and heparin. Although best known for their role in allergy and anaphylaxis, mast cells play an important protective role as well, being for example intimately involved in wound healing and defense against pathogens.

Mast cells are present in most tissues characteristically surrounding blood vessels and nerves, and are especially prominent near the boundaries between the outside world and the internal milieu, such as the skin, mucosa of the lungs and digestive tract, as well as in the mouth, conjunctiva and nose.

In allergic reactions, mast cells remain inactive until an allergen binds to IgE already in association with the cell. Other membrane activation events can either prime mast cells for subsequent degranulation or can act in synergy with FceRI signal transduction. Histamine from such granulation dilates post capillary venules, activates the endothelium, and increases blood vessel permeability. Histamine release leads to local edema (swelling), warmth, redness, and the attraction of other inflammatory cells to the site of release. It also irritates nerve endings (leading to itching or pain). Cutaneous signs of histamine release are the "flare and wheal"-reaction. The bump and redness immediately following a mosquito bite are a good example of this reaction, which occurs seconds after challenge of the mast cell by an allergen. The other physiologic activities of mast cells are much less well-understood. Several lines of evidence suggest that mast cells may have a fairly fundamental role in innate immunity—they are capable of elaborating a vast array of important cytokines and other inflammatory mediators such as TNFα, the) express multiple "pattern recognition receptors" thought to be involved in recognizing broad classes of pathogens, and mice without mast cells seem to be much more susceptible to a variety of infections.

Considering the toxicity of bacterial histamine in foods and the fact that it is recommended to avoid histamine-producing strains in fermented products (see further examples in Calles-Enríquez et al. *Sequencing and Transcriptional Analysis of the Streptococcus thermophiles Histamine Biosynthesis Gene Cluster: Factors That Affect Differential hdcA Expression*; APPLIED AND ENVIRONMENTAL MICROBIOLOGY, September 2010, Vol. 76, No. 18, p. 6231-6238) it can not considered to be obvious to use certain selected *Lactobacillus* strains for local production of histamine in treatment and/or prophylaxis of various diseases.

The relationship between a host and its microbes is complex, as it also is for certain of a mammalian's own cell types, such as mast cells. This host-microbe relationship has been developing over many years of co-evolution; this includes the microbes production of various metabolites that can benefit the host nutritionally, immunologically etc., act as whole or part antagonists, agonist, de-sensitization etc. of specific receptors or other processes. There is therefore also a need to understand such specific interactions between microbes and man related to a specific disease or other situations influencing the health of the host so that the most appropriate probiotic strains can be selected and used to counteract such developments.

The inventors herein have found that a selected group of lactobacilli, including certain strains of *Lactobacillus reuteri* locally produces histamine under specific growth conditions. Such locally produced histamine, contrary to earlier belief, will benefit the host in multiple ways including reduction of inflammation, reducing certain cancers etc.

Another object of the invention is to provide products containing said strains together with a specific carbon source, in order to have a synbiotic product.

Other objects and advantages will be more fully apparent from the following disclosure and appended claims.

Administering the lactic acid bacterial strains, selected accordingly to the present method, to a mammal will result in locally produced histamine that could be beneficial for several reasons.

A primary object of the present invention is to provide a method of selecting lactic acid bacterial strains assuring good anti-inflammatory effect. These strains could preferably be used for treatment and/or prophylaxis of inflammatory conditions, since the histidine operon and the production of histamine is essential for the anti-inflammatory capacity of certain lactic acid bacterium. Preferably the strains may be used for treatment and/or prophylaxis of inflammatory processes in the GI tract, GU tract, oral cavity, in the lungs and airways, on the skin etc, of the mammalian body, including but not limited to colitis. IBD. IBS, diverticulosis, gingivitis, vaginitis etc. It is previously known that histamine via the H2 receptor can reduce the gene expression of TNF-alpha. Further, mast cells are capable of elaborating a vast array of important cytokines and other inflammatory mediators such as TNF-alpha. However it is not previously known that the histidine operon, and local histamine production of such selected strains, could be beneficial to the host and is for example a key factor in selected *L. reuteri* strains' anti-inflammatory capacity. Neither is it previously known to use *L. reuteri* selected according to the present method in treatments requiring histamine.

Preferred products and strains for the treatment and/or prophylaxis of inflammatory conditions are *Lactobacillus reuteri*, in particular *Lactobacillus reuteri* 6475 (ATCC PTA 6475). In other embodiments of the invention the strain used is not *Lactobacillus reuteri* 6475 (ATCC PTA 6475).

The therapeutic uses of the strains, products and compositions of the invention as defined herein generally result in the reduction or alleviation of the relevant disease or symptoms of disease, for example can result in a significant reduction in inflammation levels in the mammal. For example, locally produced histamine may be activating $H_2$ receptors on intestinal epithelial cells as well as immune cells to suppress host mucosal immunity, e.g. via the inhibition of pro-inflammatory cytokines. Thus, the present invention allows for the conversion of a dietary component (histidine) to histamine at the site of activity and local modulation of the host immune response (e.g. in the gut). It can be seen that such local production of histamine provided by the present invention can provide real advantages over for example oral ingestion or other forms of administration of histamine, especially given the fact that such oral ingestion would not be advocated due to the recognized toxic effects and health risks.

In particular where inflammatory diseases of the intestine are concerned, the therapeutic uses of the strains, products and compositions of the invention can result in significant reduction in ulceration and intestinal damage (e.g. colon damage) measured for example by a standard method such as a Wallace score, a significant reduction in weight loss or a significant reduction in inflammation of the intestine, e.g. the colon.

Such reduction or alleviation of disease or symptoms thereof can be measured by any appropriate assay. Preferably the reduction or alleviation of disease or symptoms is statistically significant, preferably with a probability value of <0.05. Such reduction or alleviation of disease or symptoms is generally determined compared to an appropriate control individual or population, for example a healthy mammal or an untreated or placebo treated mammal.

An appropriate mode of administration and formulation of the strains, etc., is chosen depending on the site where local production of histamine is desired. A preferred mode of administration is oral, however, equally for some treatments topical or some other form of local administration to the skin, rectum, vagina or gums will be appropriate, or intravenous or intramuscular injection will be appropriate.

Although the Examples herein demonstrate the use of strains of the invention and appropriate doses thereof to treat colitis, it will be appreciated that this is only one example of the inflammatory conditions which can be treated in accordance with the present invention and that appropriate doses of the strains, products and compositions of the invention as defined herein can be chosen depending on the disease to be treated, the mode of administration and the formulation concerned.

Dietary mixtures comprising histidine may be used to ensure the presence of histidine and thereby increase the efficacy of the bacteria. Histidine may be administered alone or together with the bacteria.

One possibility to ensure the bacteria's supply of histidine is to eat histidine rich food, including but not limited to soy protein, cheese, egg, chicken and pork.

The histidine operon in bacteria has been shown to improve the growth capacity under conditions of low pH or energy source limitation (Calles-Enriquez et al.) but the histidine operon has not been associated with anti-inflammatory features of certain L. reuteri strains.

It is another object of the present invention to use the strains selected according to the present method in cancer therapy. Histamine in combination with IL-2 has been used for treatment of AML. Using the strains of the present invention will result in locally produced histamine that in combination with IL-2 could be used for treatment of AML.

Another object of the present invention is to use the selected strains in order to reduce food allergy, other allergic reactions or other autoimmune diseases. Systemic increases in histamine are as previously known a consequence of allergy by the granulation of mast cells. When administering strains selected according to this invention to a recipient, the locally produced histamine will lead to a desensitization effect that will reduce allergy or other autoimmune diseases.

It is also an object of the present invention to use the histamine-producing lactic acid bacteria strains to reduce the risk of traveler's diarrhea. Patients treated with histamine blockers have an increased risk of getting traveler's diarrhea; this increased risk could be neutralized by administrating the lactic acid bacteria selected according to the present method.

Yet another object of the present invention is to use the selected strains in treatment of MS. Histamine has been proposed to be an important molecule for developing new treatments for MS and the strains selected accordingly to the present invention will provide the patient with histamine.

Yet another object of the present invention is to use histamine-producing bacteria as a skin-anti-inflammatory treatment using available histidine and histidine analogs in the skin. Since histidine is a substrate for urocanic acid which the skin produces by UV irradiation and the urocanic acid has anti-inflammatory properties on the skin.

It is another object to use such selected strains to inhibit activation of ERK1/2.

Another object of the invention is to inhibit TNF alpha.

Another object of the invention is to reduce inflammation, locally or systemically.

Another object of the invention is to enhance synaptic vesicle exocytosis by inhibiting ERK1/2.

Another object of the invention is to promote human embryonic stem cell self-renewal by inhibiting ERK1/2.

Another object of the invention is to induce macrophage ABCA1 expression and cholesterol efflux by inhibiting ERK1/2.

Another object of the invention is to reduce cardiac hypertrophy and heart failure by inhibiting ERK1/2.

Another object of the invention is to reduce the proliferation of certain cancers including leukemia (for example AML) or malignant melanoma. Thus, such cancers are preferred diseases which could be treated using the strains, products and compositions of the present invention.

Another object of the invention is to use selected strains to produce histamine under certain conditions as a neurotransmitter for example in GU tract interactions with the CNS, and also neural signaling in local pain. This role as a neurotransmitter can be extended to effects on intestinal motility (to treat constipation or diarrhea) and to pain signaling in the gut.

Another object of the invention is to use selected strains for influencing the gut-brain axis as the selected lactic acid bacteria (LAB) will produce histamine and affect visceral pain perception and signaling in the enteric nervous system. Thus, it can be seen that the present invention can be used for the treatment and/or prophylaxis of any disease which will benefit from local histamine production or the treatment and/or prophylaxis of any disease which can be treated with the local administration of histamine.

It is a further object of the invention to provide products containing said strains.

It is a further object of the invention to provide products containing said strains together with a specific carbon source, in order to have a synbiotic product, which will through specific stimulation of the histamine-producing strain, enhance the effects.

It is a further object of the invention to provide products comprising the said strains together with histidine, including histidine analogs or histidine contained in products or compositions. Preferably such a mixture is administered orally in a protective capsule for release of the content in the lower GI tract to ensure survival of both the histidine and the bacteria at the site of action.

It is a further object of the invention to combine administration of said strains with a histidine rich diet.

A yet further aspect of the invention provides a product for the therapeutic uses as defined elsewhere herein, wherein said use further comprises the administration of at least one further therapeutic or nutritional agent. In such embodiments, the further therapeutic agent can be any further agent which is useful in the treatment of the disease in question, for example is a further anti-inflammatory agent or an immunotherapeutic agent such as for example a chemokine or cytokine (e.g. IL-2).

In preferred embodiments, said further agent comprises histidine or a histidine analog, an appropriate carbon source which supports the production of histamine by the bacterial strain, or a combination thereof.

Said further agents can be administered together with the strains of the invention or can be administered separately. In addition, said further agents can be administered at the same time as the strains of the invention or at different time points. Suitable administration regimes and timings can readily be determined by the skilled person depending on the further agent in question.

The present invention also provides a composition comprising:
(i) a lactic acid bacterial strain obtainable by the selection method of the invention (or a lactic acid bacterial strain capable of producing histamine as otherwise defined herein), wherein said lactic acid bacterial strain has an active histidine operon and is capable of producing histamine; and
(ii) at least one additional component selected from the group consisting of an appropriate carbon source which supports the production of histamine by said strain, a source of histidine or histidine analog, and a combination thereof.

In products, compositions and uses of the invention as described herein, preferably said histidine or histidine analog is in the form of a histidine or histidine analogy contained in a foodstuff or food supplement, or said carbon source comprises glucose. Preferably said carbon source will not comprise sucrose, or at least will only comprise sucrose at such a level which will not significantly compromise histamine production by the strain. Optionally, sources of other amino acids can also be provided.

In alternative embodiments, the strains as defined in part (i) can be combined with a further component which is useful in the treatment of the disease in question, i.e. a further therapeutic agent, for example a further anti-inflammatory agent or an immunotherapeutic agent such as for example a chemokine or cytokine (e.g. IL-2).

*Lactobacillus reuteri* is a heterofermentative lactic acid bacterial species that naturally inhabits the gut of humans and animals. Specific probiotic *L. reuteri* strains potently suppress human TNFα production while other probiotic *L. reuteri* strains enhance human TNFα production.

The invention herein is made possible by mechanistic studies of probiotic *L. reuteri* strain 6475 and other strains which have demonstrated their effect upon activated human myeloid cells. *L. reuteri* metabolites were isolated using HILIC-HPLC, and histamine was identified by NMR spectroscopy and mass spectrometry. Quantification of histamine by triple quadrupole MS revealed that *L. reuteri* strain 6475 produces relatively high concentrations of histamine when grown in a glucose-based minimal media. Previous transcriptomics studies had suggested that two genes in the *L. reuteri* histidine operon may play a role in TNF inhibition by strain 6475. Targeted mutagenesis of these genes revealed that each gene in the histidine operon, the histidine; histamine antiporter, HdcA, and HdcB, are important for the TNF-inhibitory phenotype of strain 6475. Mechanistic studies demonstrated that histamine is inhibiting TNF via signaling through the $H_2$ but not $H_1$ receptor. Signaling through the $H_2$ receptor increases intracellular cAMP, which activates PKA. PKA activity is necessary for TNF suppression by histamine. Histamine blocks activation of the MEK-ERK MAPK signaling pathway.

Histamine is better known for its pro-inflammatory effects in allergy and anaphylaxis, but several studies have demonstrated anti-inflammatory functions of histamine. In vitro studies have shown that histamine can inhibit production of pro-inflammatory cytokines. IL-1, IL-12, and TNF from LPS-stimulated human monocytes and macrophages and this effect is reversed by $H_2$ receptor antagonists. Additionally, histamine can stimulate production of the anti-inflammatory cytokine, IL-10, via the $H_2$ receptor. Signalling through the $H_2$ receptor results in decreased expression of the CD14 receptor, a receptor involved in LPS recognition, on the surface of human monocytes. The TNF receptor is also affected by histamine. Signalling through the $H_1$ receptor induces shedding of both the TNFR1 and the TNFR2. In vivo studies have also revealed an anti-inflammatory role for histamine. Treatment with dimaprit, a specific $H_2$ receptor agonist, reduced plasma TNF levels in mouse models of endotoxin shock (LPS challenge) and hepatitis (LPS plus galactosamine challenge). Histamine was protective in an LPS-induced liver injury mouse model, and these effects were attenuated in an $H_2$ receptor knock-out mouse. In the gut, histamine may help protect against bacterial infection. Signalling through the $H_2$ receptor in Peyer's patches helps prevent infection by *Yersinia enterocolitica*.

The effect of histamine can be determined by the expression of histamine receptors on the target cell. In T-cells, the effect of histamine is dependent on which histamine receptor is activated.

By signalling through the $H_1$ receptor, histamine enhances $T_H1$-type responses but suppresses both $T_H1$ and $T_H2$ responses via the $H_2$ receptor. A study was performed looking at histamine receptor expression in the human gastrointestinal tract. Many of the cell types examined expressed multiple histamine receptors. For example, immune cells, including macrophages, highly expressed the $H_1$ and $H_2$ receptor and demonstrated low expression of the $H_4$ receptor. Increased mast cells and histamine have been implicated in the visceral hypersensitivity associated with IBS. The increased number and activity of mast cells near colonic mucosal innervation may result in heightened abdominal pain perception. A study with ketotifen, a mast cell stabilizing agent, demonstrated an increased pain threshold in patients with IBS, decreased IBS symptoms, but no change in the number or activity (determined by histamine and tryptase release) of mast cells in rectal biopsy tissue. The effects of ketotifen in improving IBS may not be the result of stabilizing mast cells, but could be attributed to its other role as an $H_1$ receptor antagonist. If activation of the $H_1$ receptor is associated with a pro-inflammatory response, blocking its activity with ketotifen can allow histamine produced either by mast cells or the gut microbiota, such as *L. reuteri*, to signaling through the $H_2$ receptor only. As we have demonstrated, signaling via the $H_2$ receptor can suppress TNF production and cause an anti-inflammatory effect. This ketotifen mechanism can be used for new therapies combining H1 receptor antagonists with general probiotic effect of a *L. reuteri* strain.

Further changing the carbon source of the growth media from glucose to sucrose is sufficient to suppress the TNF-inhibitory phenotype of a selected strain, for example *L.* reuteri strain 6475. In addition, significant down-regulation of all three genes in the histidine operon was observed with the sucrose growth condition.

The identification of histamine as an anti-inflammatory compound produced by selected probiotic *Lactobacillus* strains will help determine therapeutic applications for such strains. Mechanistic studies linked the activation of the $H_2$ receptor on THP-1 cells with histamine and the suppression of ERK activation. ERK activation is involved in many cellular functions besides TNF production. ERK activation is involved in proliferation, tumorigenesis, differentiation, and cell survival. The results suggest a role for selected strains such as *L. reuteri* 6475 in protecting against cancer by suppressing inflammation, cell proliferation, and apoptosis via inhibition of ERK activation. In addition, histamine is a known neurotransmitter. Production of histamine by selected strains can influence signalling in the enteric nervous system, impacting pain perception and gut motility. To ensure the production of histamine at the site of action it may be advantageously to provide the bacteria with histidine. Histidine may be administered together with the bacteria or alone, diets rich in histidine may increase the histamine production as well.

The present invention provides certain strains of lactic acid bacteria and a method of selecting such strains and products comprising such strains. The bacteria are selected using a screen for the histidine operon; surprisingly the presence of an active histidine operon has been shown to be essential for various beneficial effects such as the immunomodulatory properties of lactic acid bacterial strains.

Other objects and advantages of the present invention will become obvious to the reader and it is intended that these objects and advantages are within the scope of the present invention.

The invention will be further described with reference to the following non-limiting Examples:

EXAMPLES

TABLE 1

Bacterial strains used in this study

| Bacterial Strains | Description | Source |
| --- | --- | --- |
| *L. reuteri* ATCC PTA 6475 | Isolate from Finnish mother's milk | BioGaia AB (Raleigh, NC) |
| *L reuteri* ATCC PTA 6475::JP577 | insertional mutant | This study |
| *L. reuteri* ATCC PTA 6475::1229 | insertional mutant | This study |
| *L. reuteri* ATCC PTA 6475::1230 | insertional mutant | This study |
| *L. reuteri* ATCC PTA 6475::1231 | insertional mutant | This study |

TABLE 2

Transcriptomic analysis of the histidine operon in *L. reuteri* strain 6475 mutants

| | HdcB gene | | Histidine decarboxylase, pyruvoyl type A (HdcA) | | Histidine/ Histamine Antiporter | |
| --- | --- | --- | --- | --- | --- | --- |
| Comparison | Fold Change | p Value | Fold Change | p Value | Fold Change | p Value |
| CFAS*(23)/6475 | −2.3 | <0.05 | −1.1 | 0.68 | −1.2 | 0.36 |
| THFS1*/6475 | −1.33 | 0.60 | −3.28 | <0.05 | −3.45 | <0.001 |

TABLE 2-continued

Transcriptomic analysis of the histidine operon in *L. reuteri* strain 6475 mutants

| | HdcB gene | | Histidine decarboxylase, pyruvoyl type A (HdcA) | | Histidine/ Histamine Antiporter | |
| --- | --- | --- | --- | --- | --- | --- |
| Comparison | Fold Change | p Value | Fold Change | p Value | Fold Change | p Value |
| Sucrose§/Glucose | −11.8 | <0.01 | −30.1 | <0.001 | −5.5 | <0.001 |
| THFS2/6475 | — | — | 1.2 | 0.7 | 0.8 | 0.2 |
| PocR/6475 | — | — | 2.4 | 0.10 | 1.3 | 0.66 |

*Insertion mutants that lose the ability to inhibit TNF production compared to the wild-type strain 6475. CFAS: cyclopropane fatty acid synthase. THFS1: tetrahydrofolate synthase1, THFS2: tetrahydrofolate synthase 2.
§Wild-type 6475 grown in LDMIIIS compared to wild-type 6475 grown in LDMIIIG. Wild-type 6475 grown in LDMIIIS loses the ability to inhibit TNF production.

Example 1

Production of Histamine by Selected *Lactobacillus* Bacterial Strains and Culture Conditions All bacterial strains used in this study are described in Table 1. *Lactobacillus reuteri* ATCC PTA 6475 is an isolate from Finnish mother's milk (BioGaia AB, Raleigh, N.C.). This strains is available to the public at the American Type Culture Collection (Rockville, Md.) having been deposited there on Dec. 24, 2004. This deposit meets the requirements of the Budapest Treaty.

*L. reuteri* strains ATCC PTA 6475, ATCC 6475 JP577. ATCC 6475 1229, ATCC 6475 1230, and ATCC 6475 1231 will be referred to as strains 6475, JP577, 1229, 1230, and 1231, respectively, throughout this disclosure. *L. reuteri* strains were cultured under anaerobic conditions for 16-18 h in deMan, Rogosa, Sharpe media (Difco, Franklin Lakes, N.J.), and inoculated into 2 L of a semi-defined media, LDMIII ($OD_{600}$ adjusted to 0.1), which has been described previously. The carbon source was either glucose, LDMIIIG, or sucrose, LDMIIIS. The culture was grown for 24 h at 37° C. in an anaerobic workstation (MACS MG-500, Microbiology International. Frederick, Md.) supplied with a mixture of 10% $CO_2$, 10% $H_2$, and 80% $N_2$. Samples were taken at different times to follow the growth by measuring $OD_{600}$. At stationary phase (24 h), the cells were pelleted from the 2 L culture (4000×g, 10 min). Cell pellets and bacteria cell-free supernatants were stored at −20° C. before further processing for HPLC separation and testing in a TNF inhibition bioassay.

Cell Line and Reagents

In vitro experiments were performed with THP-1 cells (human monocytoid cell line, ATCC. Manassas, Va.) maintained in RPMI (ATCC) and heat-inactivated fetal bovine serum (Invitrogen, Carlsbad, Calif.) at 37° C., 5% $CO_2$. MEK1/2, phospho-MEK1/2, ERK1/2, and phospho-ERK1/2 antibodies and MEK inhibitor U0126 were received from Cell Signaling Technology (Danvers, Mass.), and the β-Actin antibody was received from Abcam (Cambridge, Mass.). All other reagents were received from Sigma (St. Louis, Mo.) unless otherwise stated.

HILIC-HPLC Separation of Cell Wall Associated Factors

Cell pellets (7 g) from strain 6475 grown in either LDMIIIG or LDMIIIS were washed with 30 mL ice cold 50% acetonitrile/0.1% trifluoroacetic acid (TFA). The cell suspension was centrifuged for 10 min, 4000×g at 4° C. Supernatants were filtered through polyvinylidene fluoride (PVDF) membrane filters (0.45 μm pore size, Millipore, Bedford, Mass.), lyophilized, and resuspended in 10 mL 0.1% formic acid. The resuspended sample was size fractionated with Amicon Ultra-15 centrifugal filter units using ultracel-3 membrane (Millipore, Bedford, Mass.). The filtrate (9 mL) was dried down to 1 mL with a speed vacuum, and 0.75 mL was used for HILIC-HPLC. The sample was dissolved with 100% acetonitrile before running on a PolyLC Hydroxyethyl column with a gradient of 100-0% acetonitrile, 0.1% formic acid. The sample was run for 25 min and 25 fractions (A1—C1) were collected at 10 mL/min/ tube. Three milliliters from each fraction was lyophilized, resuspended in 3 mL 0.1% acetic acid, and lyophilized again for testing in a TNF inhibition bioassay TNF Inhibition Bioassay and TNF ELISA Bacterial supernatants (10 mL) from a 24 h LDMIII culture were filter-sterilized using PVDF membrane filters (0.22 μm pore size, Millipore) and size fractionated as described above. One milliliter of the <3 kDa filtrate was speed vacuum dried and resuspended in RPMI media. These processed supernatant samples are termed conditioned media. All supernatants were normalized by volume to an $OD_{600}=1.0$. Lyophilized fractions from the HILIC-HPLC separation were resuspended in 400 μL 10 mg/mL ammonium bicarbonate, speed vacuum dried, and resuspended in 400 μL RPMI media. Conditioned media and cell pellet wash fractions were tested for their ability to modulate TNF production in monocytoid cells. In brief, THP-1 cells (approximately $5 \times 10^4$ cells) were stimulated to produce TNF by the addition of 100 ng/mL $Pam_3Cys$-SKKKK×3 HCl (EMC Microcollections, Tuebingen, Germany) as previously described. Inhibitors—$H_2$ receptor antagonists, ranitidine and cimetidine ($10^{-4}$-$10^{-6}$ M), $H_1$ receptor antagonist, indomethacin ($10^{-5}$-$10^{-6}$ M), MEK inhibitor, U0126 (10 μM), and PKA inhibitor, H89 (N-[2-(p-bromocinnamylamino) ethyl]-5-isoquinolinesulfonamide dihydrochloride) ($10^{-5}$ M)—were added to the THP-1 cells followed by L. reuteri conditioned media or cell pellet wash fractions (5% v/v), histamine ($10^{-5}$ M), or dibutyryl cAMP ($10^{-3}$-$10^{-7}$ M). Plates were incubated at 37° C. and 5% $CO_2$ for 3.5 h. THP-1 cells were pelleted (3000×g, 5 min. 4° C.), and quantitative ELISAs were used to determine TNF quantities in THP-1 cell supernatants according to the manufacturer's instructions (R&D Systems, Minneapolis, Minn.).

L. reuteri 6475 TNF-Inhibitory Compound(s) were Isolated Using Hydrophilic Interaction Liquid Chromatography—High Performance Liquid Chromatography (HILIC-HPLC)

Bacterial cell pellets were washed to remove compounds loosely associated with the cell surface. Components of the cell pellet wash were separated based on hydrophobicity using HILIC-HPLC, and the resulting 25 fractions were tested for retention of the TNF-inhibitory compound. L. reuteri 6475 grown in a minimal media with glucose as the sole carbon source produces TNF-inhibitory factors that were retained in 3 separate HILIC-HPLC fractions (B3. B5 and B6, data not shown). L. reuteri 6475 grown with sucrose as the sole carbon sources loses the TNF-inhibitory phenotype and served as the negative control. None of the HILIC-HPLC fractions from the 6475 sucrose cell pellet wash demonstrated significant TNF inhibition (data not shown). Histamine was Identified in a TNF-Inhibitory HILIC-HPLC Fraction by NMR Spectroscopy and Mass Spectrometry TNF-inhibitory HILIC-HPLC fraction B3 was analyzed by $^1H$ NMR and compared to the neighboring non-TNF inhibitory fraction B4. A unique series of peaks with a chemical shift between 7.0-7.5 ppm, which is characteristic of an aromatic compound, was observed in fraction B3 but not fraction B4 (data not shown). This aromatic compound cluster was further analyzed with heteronuclear single quantum coherence (HSQC) 2-dimensional (2D) NMR in order to identify its components. The aromatic compounds consisted of tryptophan, phenylalanine, histamine, and one compound that was unidentifiable. Tryptophan and phenylalanine are components of the bacterial growth media while histamine is not. These results were confirmed using an additional 2D NMR method, total correlation spectroscopy (TOCSY). Histamine is a biogenic amine that is produced from histidine via the histidine decarboxylase by some fermentative bacteria including lactobacilli. Histamine was also identified in fraction B3 using electrospray time-of-flight mass spectrometry (ESI TOF MS). Histamine is not covalently modified based on its fragmentation pattern in MS/MS analysis. Analysis of the corresponding B3 fraction of L. reuteri 6475 grown in a sucrose media with ESI TOF MS did not reveal any histamine. L. reuteri 6475 grown in a glucose media produces histamine, which is present in a TNF-inhibitory HILIC-HPLC fraction.

Figure 1:
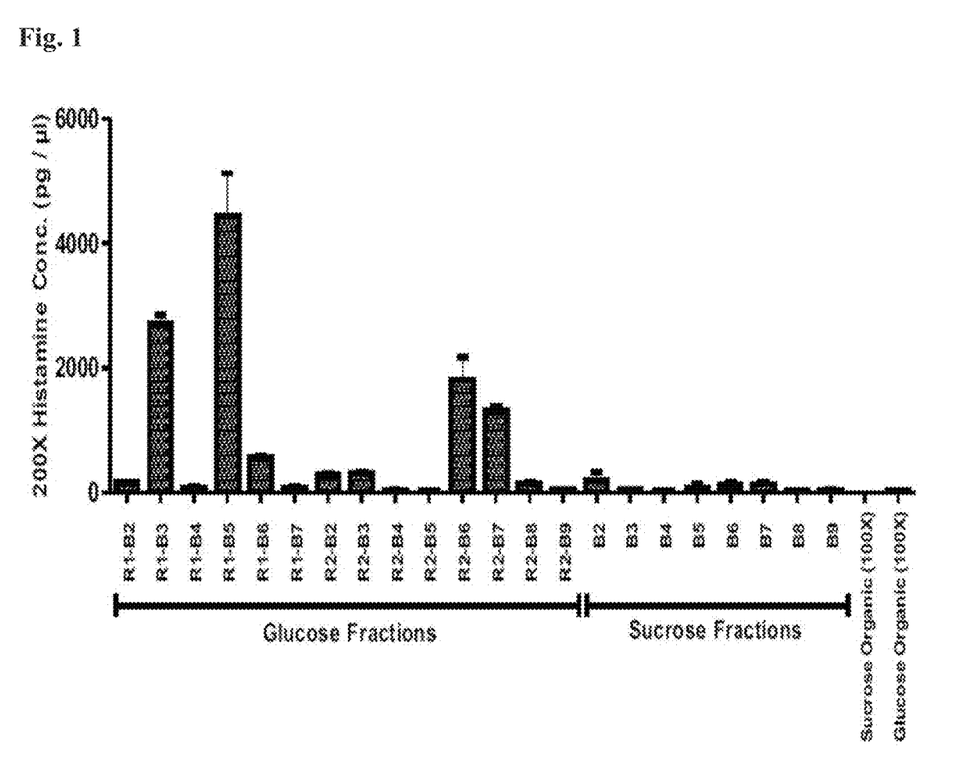
FIG. 1—Quantification of histamine in HILIC-HPLC fractions. Triple quadrupole mass spectrometry was used to quantify histamine present in a select range of HILIC-HPLC fractions. TNF-inhibitory fractions had the highest amounts of histamine out of all the fractions examined.

Histamine was Quantified in Select HILIC-HPLC Fractions Using Triple Quadrupole Mass Spectrometry Triple quadrupole mass spectrometry is an established, highly sensitive method of quantifying small molecular compounds. Histamine was quantified in a select range of HILIC-HPLC fractions from L. reuteri 6475 glucose (B2-B7) and sucrose (B2-B9) as well as the bacterial culture supernatant. High levels of histamine (>300 ng/mL) correlated with the ability of the HILIC-HPLC fractions to inhibit TNF (FIG. 1). Low levels of histamine were measured in most fractions examined, including those from 6475 sucrose (FIG. 1). The ability of histamine to inhibit TNF production appears to be concentration dependent.

Figure 2A:
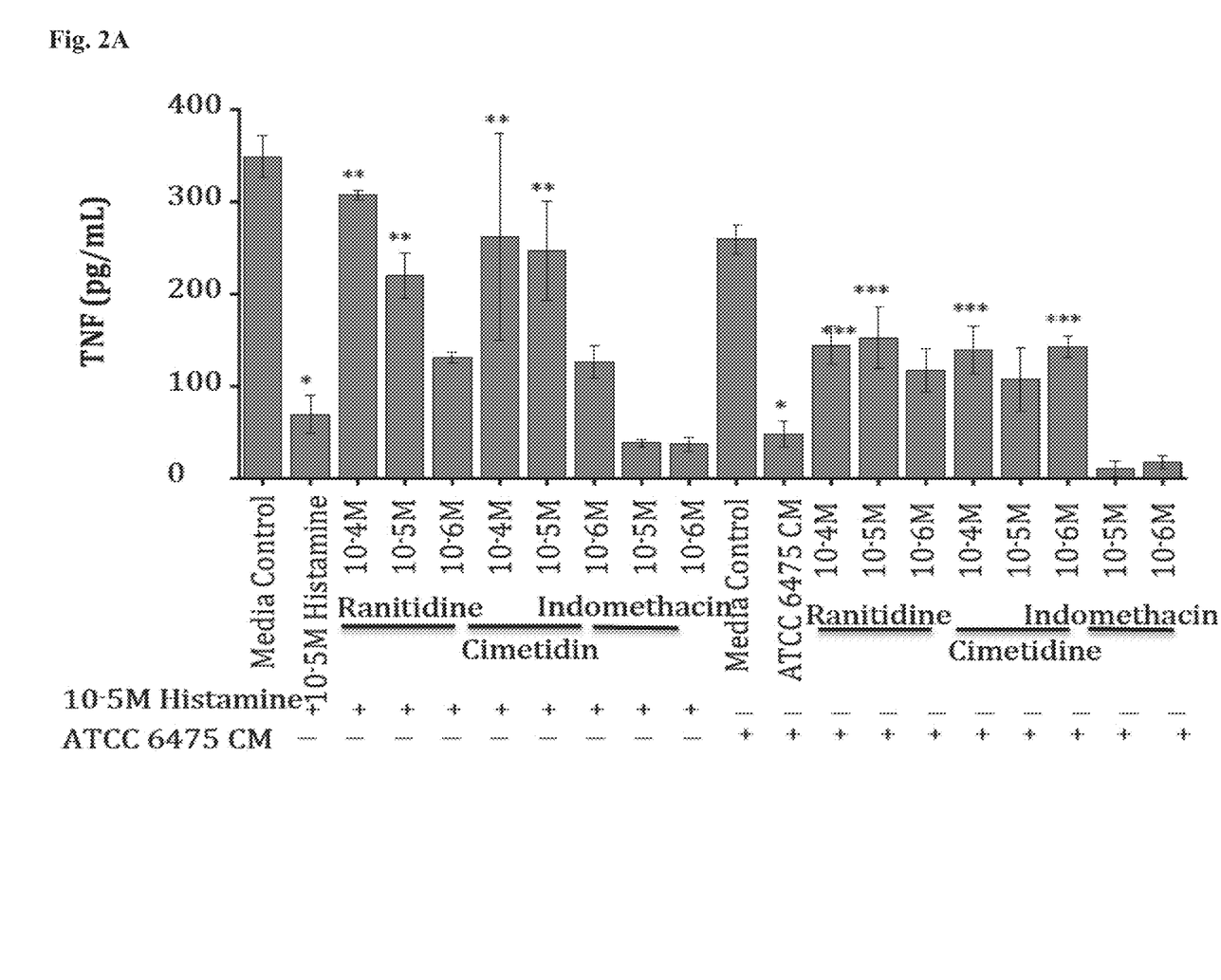
FIGS. 2A-2B—Purified histamine and histamine from *L. reuteri* 6475 inhibit TNF production via the histamine $H_2$ receptor. (A) Purified histamine significantly inhibited TNF production, an effect that is blocked by specific $H_2$ receptor antagonists in a dose-dependent manner. Conditioned media (or supernatant) containing secreted factors from strain 6475 (including histamine) significantly inhibited TNF production, an effect that is partially blocked by specific $H_2$ receptor antagonists. N=3, *p value <0.05 compared to media control, p value <0.05 compared to histamine, *p value <0.05 compared to ATCC 6475 conditioned media (CM). (2) The cell pellet wash from strain 6475 containing histamine suppressed TNF production, an effect that was partially blocked by specific $H_2$ receptor antagonists. Fraction B3, which contains relatively pure histamine, inhibited TNF production, an effect that was completely blocked by specific $H_2$ receptor antagonists. N=3, *p value <0.05 compared to media control, p value <0.05 compared to ATCC 6475 cell pellet wash (CP), *p value <0.05 compared to fraction B3.
Figure 2B:
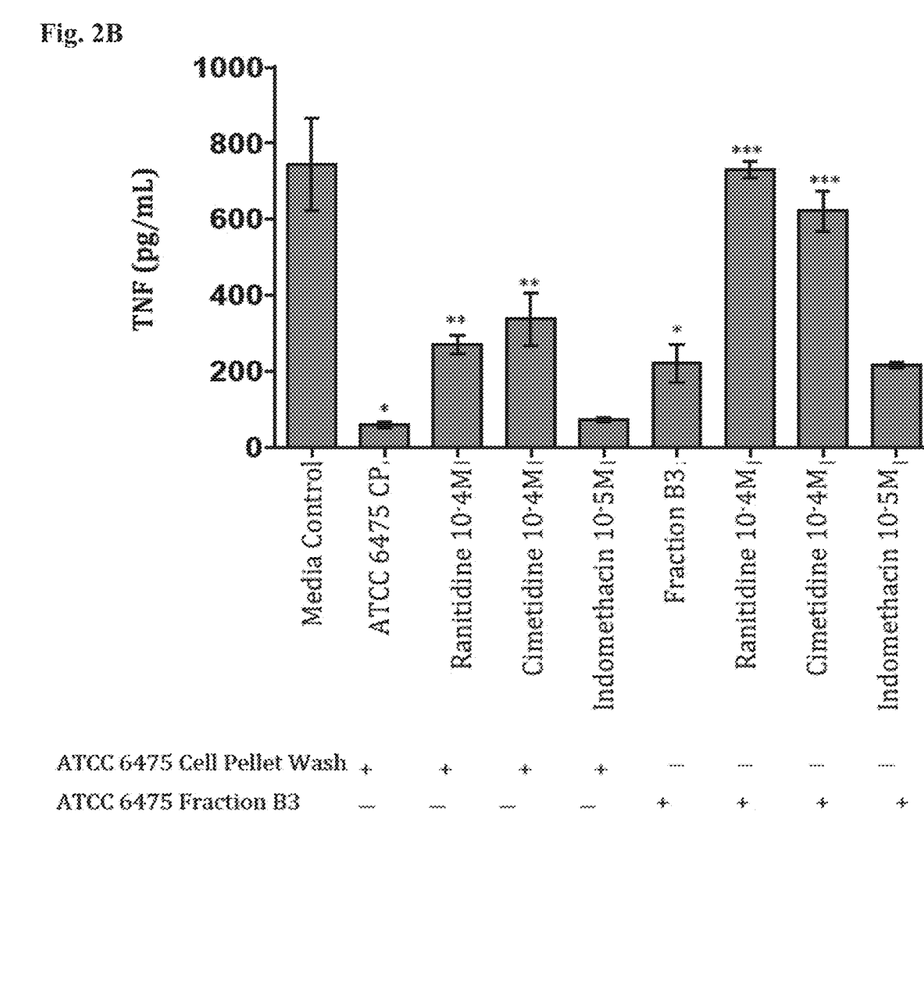
Figure 4:
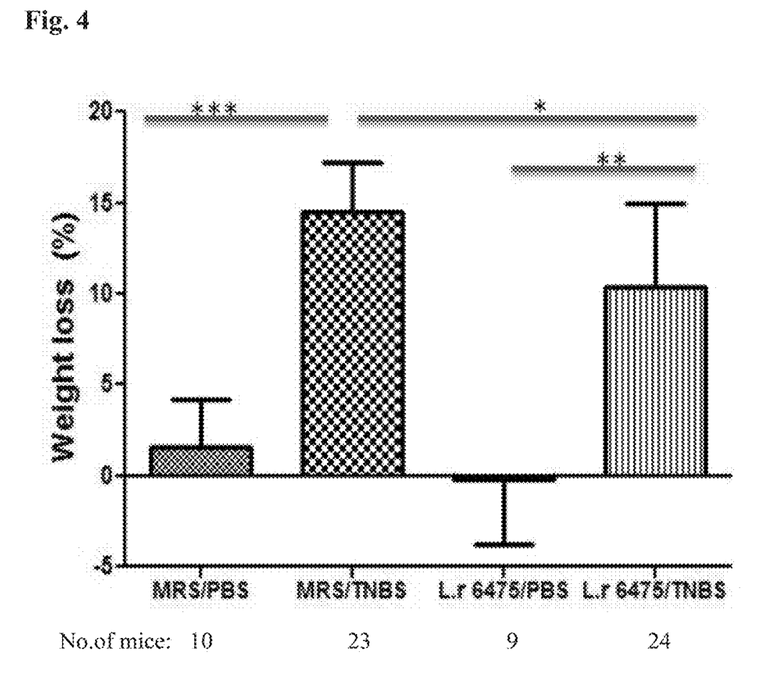
FIG. 4—*L. reuteri* 6475 significantly reduced weight loss induced by TNBS challenge, the figure represents data from two independent experiments, * p<0.05,  p<0.01, * p<0.001.

Synthetic Histamine and Histamine Produced by L. reuteri 6475 Inhibit TNF Production Via the $H_2$ Receptor Histamine can significantly inhibit TNF production from TLR2-activated human monocytoid cells (THP-1) (FIG. 4A). Histamine can signal through four different histamine receptors, however, monocytoid cells express high levels of the $H_1$ and $H_2$ receptors only. Previous studies have shown effects of histamine on TNF production via the $H_2$ receptor. $H_1$ and $H_2$ receptor-specific antagonists were used to determine which receptor was mediating the effect of histamine on THP-1 cells. $H_2$ receptor-specific antagonists, ranitidine and cimetidine, could block TNF-inhibition by histamine in a concentration dependent manner (FIG. 2A). Flow cytometry analysis with $H_2$ receptor-specific antibodies revealed that THP-1 cells highly express the $H_2$ receptor (data not shown). An $H_1$ receptor-specific antagonist, indomethacin, had no effect on TNF-inhibition by histamine (FIG. 2A). Histamine blocks TNF production from TLR2-activated THP-1 cells via signaling through the $H_2$ receptor. L. reuteri 6475 conditioned media containing histamine significantly inhibits TNF compared to the media control, and this effect is partially blocked by $H_2$ receptor but not $H_1$ receptor antagonists (FIG. 2A). A partial block in TNF suppression indicates that histamine present in 6475 conditioned media is signaling via the $H_2$ receptor but that other TNF-inhibitory factors that act through alternative mechanisms may also be present in the conditioned media. The cell pellet wash containing histamine of strain 6475 also suppresses TNF production (FIG. 2B). As seen with 6475 conditioned media, $H_2$ receptor antagonists partially block the effect of the 6475 cell pellet wash (FIG. 2B), suggesting multiple immunomodulins are present in the unfractionated cell pellet wash. The effects of TNF-inhibitory fraction B3, which contains high amounts of purified histamine, were completely blocked by the addition of $H_2$ receptor antagonists (FIG. 2B).

Example 2

Selection of Strains Producing Histamine
Identification/Selection of Histamine-Producing Bacteria Strains to be tested and possibly selected were cultured under anaerobic conditions for 16-18 h in deMan, Rogosa, Sharpe media (Difco. Franklin Lakes, N.J.), and inoculated into 2 L of a semi-defined media, LDMIII ($OD_{600}$ adjusted to 0.1). The carbon source was glucose, LDMIIIG. Each culture was grown for 24 h at 37° C. in an anaerobic workstation (MACS MG-500, Microbiology International, Frederick, Md.) supplied with a mixture of 10% $CO_2$, 10% $H_2$, and 80% $N_2$. Samples were taken at different times to follow the growth by measuring $OD_{600}$. At stationary phase (24 h), the cells were sampled for analysis using real-time PCR to test for the presence of the three genes, the histidine/histamine antiporter, HdcA, and HdcB.

For strains positive for the three genes, the levels of produced histamine are determined by triple quadrupole mass spectrometry. The strains with highest production of histamine (>250 pg/ml) are selected. Histamine production can also be evaluated and quantified by ELISAs or immunoassays.

Example 3

Demonstration of Immunomodulation
The Histidine Operon Contributes to the TNF-Inhibitory Phenotype of L. Reuteri 6475

Figure 3A:
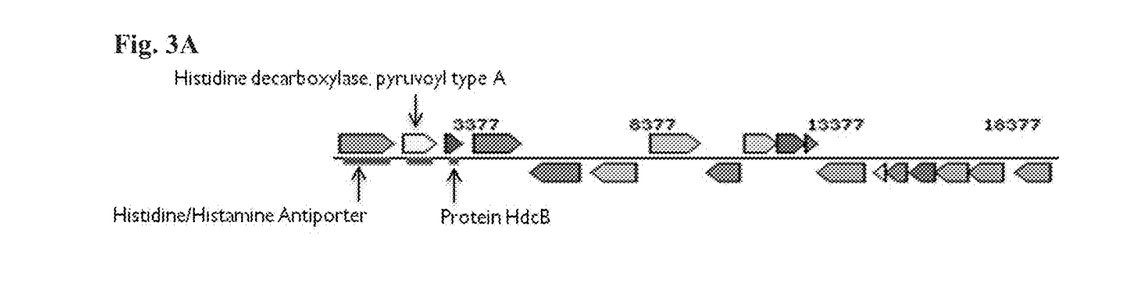
FIGS. 3A-3B—The histidine operon is important for the TNF-inhibitory phenotype of *L. reuteri* 6475. A. The histidine operon consists of three genes, the histidinetistamine antiporter, hdcA, and hdcB. B. Mutation in any one gene in the histidine operon results in a partial loss of TNF suppression by *L. reuteri* 6475. N=9, *p value <0.05 compared to media control, **p value <0.05 compared to ATCC PTA 6475.
Figure 3B:
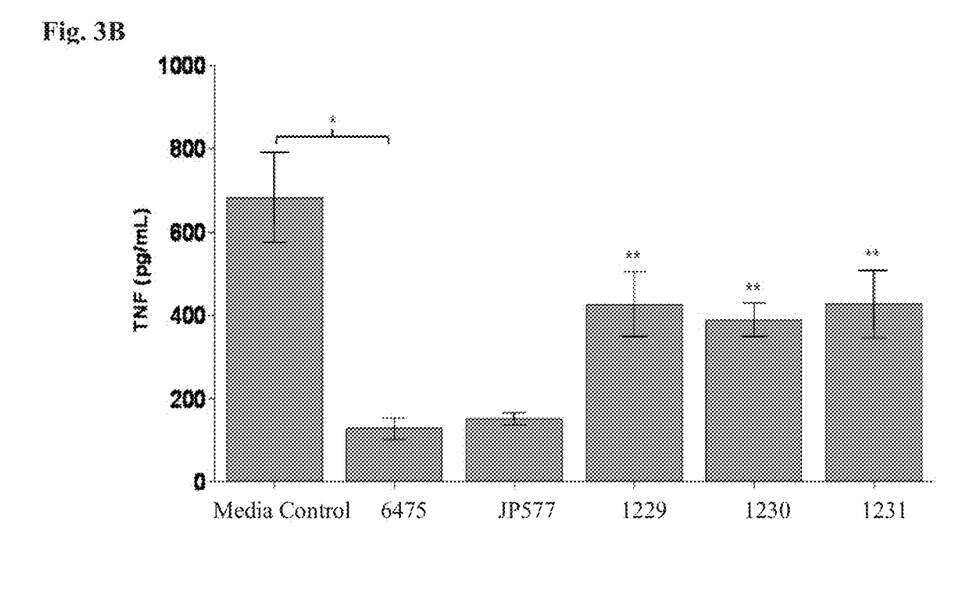

Three genes that appear to be part of an operon are involved in histamine production by L. reuteri 6475. These genes are the histidine/histamine antiporter, the histidine decarboxylase pyruvoyl type A (HdcA), and HdcB (FIG. 3A). Previous transcriptomics studies suggested that the histidine/histamine antiporter gene and HdcA were potentially important for the TNF-inhibitory phenotype of strain 6475. All 3 genes are strongly down-regulated in 6475 grown in a sucrose media (loses TNF inhibition) compared to 6475 grown in a glucose media (Table 2). In addition, at least 1 gene in the operon is down-regulated in 2 mutants that lose TNF-inhibition (Table 2). These mutants were investigated previously, and even though the gene products didn't have TNF-inhibitory properties, the genes appeared to be important for the anti-inflammatory phenotype of 6475. In contrast, 2 mutants that do not lose TNF inhibition demonstrated no down-regulation of any of the genes in the histidine operon (Table 2). Mutations were made in each of these 3 genes by inserting a premature stop codon into the gene sequence (strains 1229, 1230 and 1231). A mutation was also made in an unrelated gene, the rifampicin resistance gene, to serve as a negative control (strain JP577). A mutation in just one of the genes in the histidine operon was sufficient to cause a partial loss of TNF-inhibition compared to the wild-type strain (FIG. 3B), suggesting that each one of these genes is important for the TNF-inhibitory phenotype of L. reuteri 6475. A partial loss of activity suggests that other active immunomodulins are still being produced by L. reuteri 6475.

ERK1/2 Activation is Essential for TNF Production by TLR2-Stimulated Monocytoid Cells ERK1/2 is activated by phosphorylation from upstream MAPKK, MEK1/2, and has been shown previously to be important for TNF production. THP-1 cells were treated with a specific MEK1/2 inhibitor, U0126, for varying amounts of time prior to stimulation with a TLR2 agonist to suppress ERK1/2 activation. Treatment with U0126 for 30 min was sufficient to prevent TNF production (data not shown). ERK1/2 is activated following TLR2 stimulation and important for stimulating TNF production in our model system.

Stimulation of the $H_2$Receptor Results in Increased cAMP within the Cells

The $H_2$ receptor is a G protein linked receptor that can activate adenylate cyclase and increase intracellular cAMP. TNF can be inhibited at the level of transcription by cAMP and cAMP analogs. THP-1 cells were stimulated with a TLR2 agonist in the presence of a medium control, 6475 supernatant or histamine with or without an $H_2$ receptor antagonist and intracellular levels of cAMP were measured. L. reuteri 6475 supernatant caused a small but significant increase in cAMP (data not shown). Treatment with an $H_2$ antagonist blocked this effect. An increase in cAMP was also seen with histamine treatment, and the effect was blocked by an $H_2$ antagonist (data not shown). A synthetic analog of cAMP, dibutyryl cAMP (dcAMP), was added to TLR2-stimulated THP-1 cells and the effect on TNF production was monitored. The addition of dcAMP ($10^{-5}$-$10^{-3}$ M) was sufficient to inhibit TNF production (data not shown). Stimulation of the histamine $H_2$ receptor results in increased cAMP, which can block downstream TNF production in activated monocytoid cells.

Protein Kinase A (PKA) Activity is Important for TNF Inhibition by L. reuteri 6475, Histamine, and dcAMP Increased concentration of cAMP can activate PKA and subsequently inhibit the downstream ERK MAPK signaling pathway. To determine if PKA activity was important for TNF suppression by histamine produced by strain 6475, activated THP-1 cells were treated with a specific PKA inhibitor. H89, in the presence of 6475 supernatant, fraction B3, histamine or varying concentrations of dcAMP. The addition of H89 partially blocked TNF inhibition by all of these normally TNF-inhibitory compounds (data not shown). PKA activity is important for suppression of TNF by histamine and dcAMP.

Signaling Through the H2 Receptor Blocks Activation of MEK1/2 and ERK1/2

Previous studies have demonstrated that PKA can inhibit Ras/Raf activation of MEK and subsequently ERK MAPK signaling. Treatment of activated THP-1 cells with 6475 supernatant, histamine or U0126 blocks phosphorylation of both MEK1/2 and downstream ERK1/2 compared to the media control (data not shown). Treatment with an $H_2$ receptor antagonist restores activation of both MEK1/2 and ERK1/2 (data not shown). There was no difference in MEK1/2 and ERK1/2 protein levels with any of the treatment options. Histamine from strain 6475 inhibits activation of MEK and downstream ERK to result in decreased TNF production from TLR2-stimulated myeloid cells.

These experiments thus show that stimulation of the $H_2$ receptor results in increased cAMP, activation of Protein Kinase A (PKA) and inhibition of the MEK-ERK MAPK signaling pathway. As described above, mechanistic studies were performed to determine the effect of histamine on Mitogen Activated Protein Kinase (MAPK) signaling pathways. Inhibition of the MEK-ERK signaling pathway with a MEK-specific inhibitor is sufficient to block TNF production. Treatment of activated THP-1 cells with strain 6475 supernatant or histamine increased intracellular cAMP. The increase in cAMP was blocked by ranitidine, a specific $H_2$ receptor antagonist. Treatment of TLR2-stimulated THP-1 cells with a synthetic analog of cAMP, dcAMP, is sufficient to inhibit TNF production. Inhibition of PKA activity partially blocks TNF suppression by previously TNF-inhibitory compounds 6475 conditioned media, fraction B3, histamine, and dcAMP. Treatment of activated THP-1 cells with 6475 conditioned media, histamine, or U0126 suppressed activation of MEK1/2, an effect that was blocked in the presence of ranitidine. Treatment of activated THP-1 cells with 6475 conditioned media, histamine, or U0126 suppressed activation of ERK1/2, an effect that was blocked in the presence of ranitidine.

Example 4

MEK1/2 and ERK1/2 Detection by Western Blot

THP-1 cells were lysed in ice-cold lysis buffer consisting of 50 mM Tris, pH 7.4, 250 mM NaCl, 5 mM EDTA, 50 mM NaF, 1 mM $Na_3VO_4$, 1% v/v Nonidet P40, 0.2% v/v $NaN_3$, and protease and phosphatase inhibitors. Lysates were incubated on ice for 30 min, vortexed every 10 min, and cleared by centrifugation at 13,000×g for 10 min at 4° C. Protein concentrations were measured using the Quant-iT™ Protein Assay kit (Invitrogen) and a Qubit fluorometer according to the manufacturer's instructions. Equal amounts of proteins were loaded onto electrophoresis gels.

Analysis of ERK1/2 activation was performed using specific phospho-ERK1/2 antibodies. Cell extracts were loaded on a 10% SDS-polyacrylamide gel and transferred to polyvinylidene difluoride membranes (Bio-Rad, Hercules, Calif.). Membranes were blocked overnight at 4° C. in blocking buffer (Li-Cor Biosciences, Lincoln, Nebr.). After several washes, membranes were probed with ERK1/2, phospho-ERK1/2 or β-Actin specific antibodies diluted in blocking buffer (Li-Cor) for 1 h at room temperature. After washes, membranes were incubated with the appropriate horseradish peroxidase-conjugated secondary antibody for 1 h at room temperature, and blots were then developed using a chemiluminescent detection. Analysis of MEK1/2 activation was performed as described above except primary antibody incubation was overnight at 4° C.

Example 5 hdcA Mutant Yield Diminished Ability to Attenuate Colitis
Bacterial Strains and Culture Mutants were generated using RecT-mediated oligonucleotide recombineering. *L. reuteri* expressing RecT (strain RPRB0000) was used to construct mutations in rpoB (locus tag HMPREF0536_0828 (ZP_03961568)) and the target genes located in the histidine decarboxylase gene cluster HMPREF0536_1229 (ZP_03961969), HMPREF0536_1230 (ZP_03961970) and HMPREF0536_1231 (ZP_03961971) to yield strains RPRB3002, RPRB3004, RPRB3005 and RPRB3006, respectively. Mutations were verified by PCR, and the integrity was confirmed by sequence analysis.

*L. reuteri* ATCC PTA 6475 and histidine decarboxylase gene (hdcA) mutant were cultured in deMan. Rogosa, Sharpe (Difco, Franklin Lakes, N.J.) at 37° C. in an anaerobic workstation (MACS MG-500, Microbiology International, Frederick, Md.) supplied with a mixture of 10% $CO_2$, 10% $H_2$, and 80% $N_2$.

Preparation of *L. reuteri* Cells and Administration to Mice

A single colony of each of the *L. reuteri* strains was inoculated in 10 ml of MRS medium and grown at 37° C. under anaerobic condition for 18-20 hours. Bacteria adjusted to OD600=0.03 were inoculated into 40 ml of MRS to start the fermentation and grown at 37° C. under anaerobic condition for 5.5 hrs (OD600≈2.5, bacteria were in exponential phase at this time point). The cells were gently pelleted (2500×g, RT, 4 minutes) and resuspended in MRS at a concentration of $25×10^9$ CFU/ml. As a media control, sterile MRS medium was used. Each 8-week old female BALB/c mouse received one dose of freshly prepared wild type *L. reuteri* 6475 or hdcA mutant or MRS (0.2 ml each time) every day for seven days by orogastric gavage after 10 days of acclimatization. All mouse experiments were performed according to an approved protocol (AN-4199; animal facility of Baylor College of Medicine). Mice (45 days old) were received from Harlan Laboratories (Houston, Tex.) and maintained under specific pathogen-free conditions in filter-top cages (5 mice per cage) and had free access to distilled water and Harlan rodent chow 2918. Mice were divided into different groups randomly.

Induction of Acute Colitis Using Trinitrobenzene Sulfonic Acid (TNBS) Rectal Enema.

Colitis was induced six hours before the sixth gavage. Mice were anesthetized by constant isoflurane inhalation. A 5% TNBS solution in water (Sigma-Aldrich, USA) was diluted with equal volume of absolute ethanol and administered at dose of 100 mg/kg body weight intrarectally. Mice were kept head down in a vertical position for 2 minutes after enema to ensure complete retention of enema in the colon. Procedure control mice received 50% ethanol in PBS. Mice were weighed prior to TNBS administration and two days after TNBS administration. Then mice were sacrificed. Colonic inflammation and damage was determined by weight loss, macroscopic score and serum SAA concentration.

Macroscopic Assessment of Colitis

The colons were collected, opened longitudinally and images were recorded with a digital camera. Colonic inflammation and damage were determined according to the Wallace criteria (Morris et al., 1989). Each colon was scored blindly. Statistics were performed using GraphPad Prism version 5.01 (GraphPad Software, La Jolla, Calif.). Kruskal-Wallis test was used to detect a significant difference among all groups included in the analysis. Results were summarized as median and interquartile range.

Measurement of Serum Amyloid Protein A (SAA) as Systemic Inflammation Marker

Blood samples were collected by cardiac puncture, anti-coagulated and centrifuged for 10 minutes at 13,000 rpm to isolate plasma. Serum amyloid A (SAA) concentrations in plasma samples were measured using ELISA kits from ALPCO (Salem, N.H.) according to manufacturer's instructions. SAA is an acute phase protein indicative of systemic inflammation in mice that correlates with colitis severity.

Results

*L. reuteri* 6475 Protects Mice Against TNBS-Induced Acute Colitis

The anti-inflammatory effects of *L. reuteri* 6475 were tested in a TNBS-induced mouse model of acute colitis. Mice that received *L. reuteri* 6475 by orogastric gavage every day were compared with mice that received the media control. Mice challenged with PBS instead of TNBS were also studied as colitis negative controls.

Figure 5:
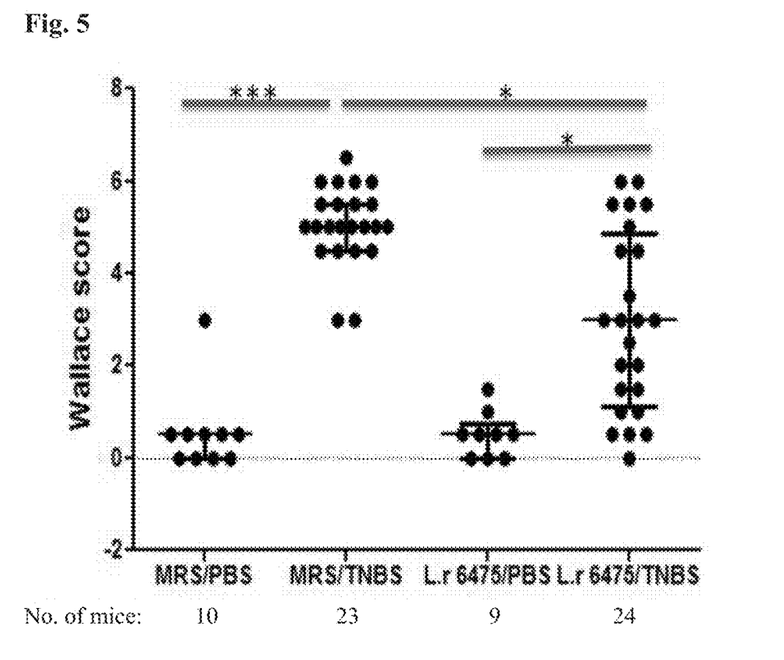
FIG. 5—*L. reuteri* 6475 significantly diminished macroscopic colon damage induced by TNBS challenge, the figure represents data from two independent experiments, *p<0.05, ***p<0.001.
Figure 6:
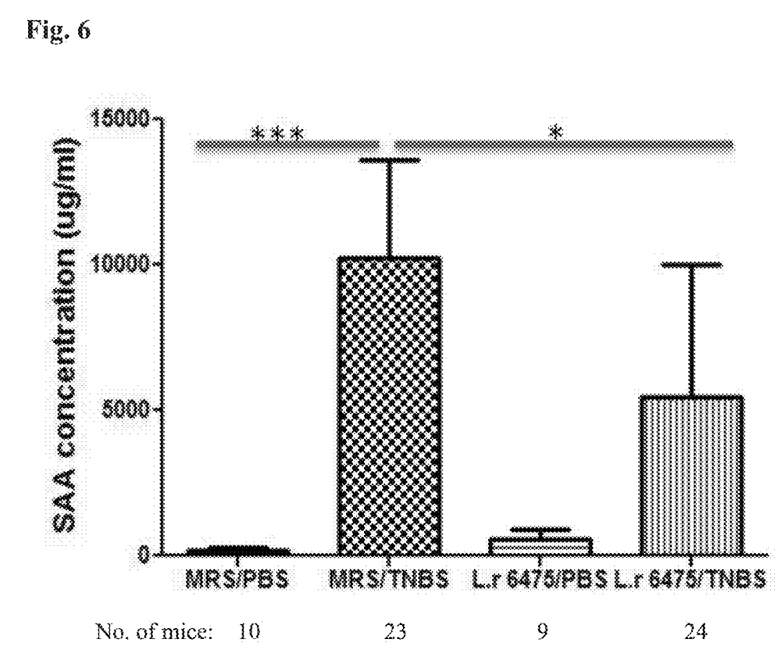
FIG. 6—*L. reuteri* 6475 significantly reduced SAA concentration induced by TNBS challenge, the figure represents data from two independent experiments, * p<0.05, *** p<0.001.

FIGS. 4-6 represent data from two independent experiments. Colitis negative controls that received PBS instead of TNBS intrarectally had very low weight loss (or even gained weight), rare colon damage and low serum SAA concentrations. Colitis positive mice that received MRS media and TNBS/ETOH developed a severe colitis characterized by a large amount of weight loss, ulceration with inflammation in the colon and the major sites of damage extending greater than 1 cm, and significantly elevated SAA concentrations in serum. Orogastric gavage with *L. reuteri* 6475 significantly reduced weight loss, macroscopic inflammation in the colon and serum SAA concentrations, showing that *L. reuteri* 6475 significantly attenuated colitis.

hdcA Mutant Yields Diminished Ability to Attenuate Colitis

Figure 7:
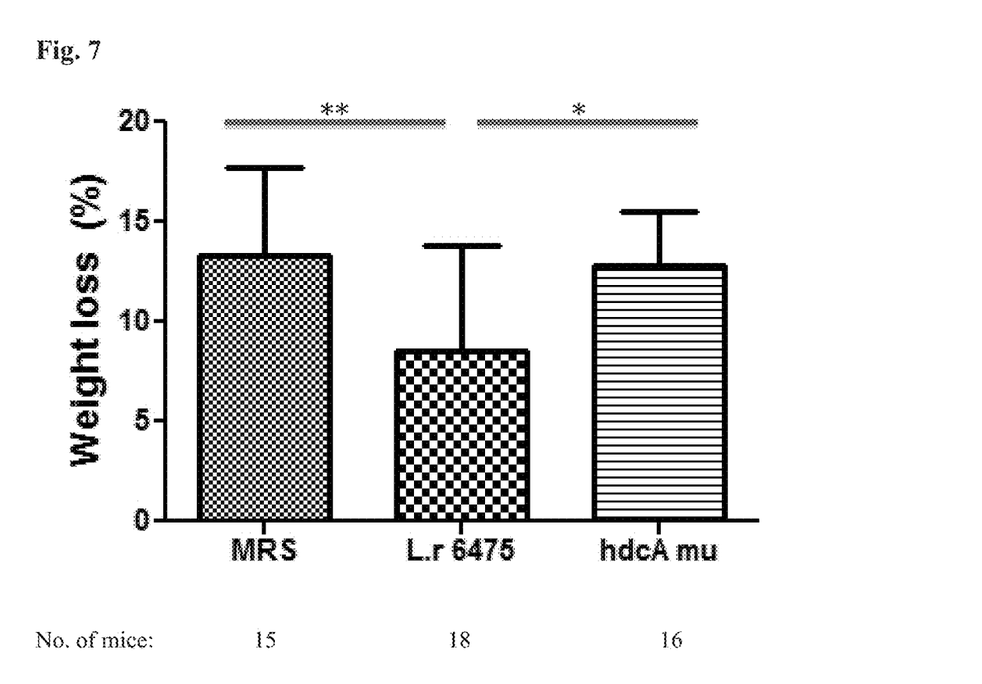
FIG. 7—hdcA mutant yielded diminished ability to attenuate colitis, the figure represents data from two independent experiments, * p<0.05, ** p<0.01.
Figure 8:
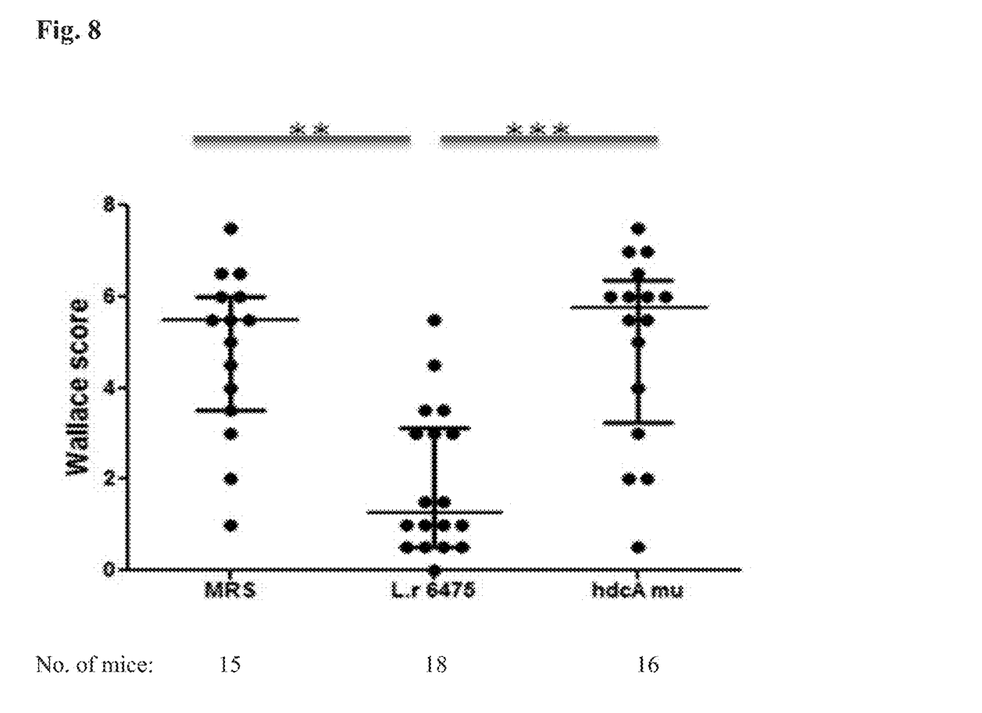
FIG. 8—hdcA mutant yielded diminished ability to attenuate colitis, the figure represents data from two independent experiments, * p<0.01, ** p<0.001.

Using the same mouse model, we tested whether hdcA gene, which encodes histidine decarboxylase was required for the anti-inflammatory effects of *L. reuteri* 6475. 8-week old female BALB/c mice were randomly divided into three groups which received wild type *L. reuteri* 6475 or hdcA mutant or MRS media respectively. FIGS. 7 and 8 represent data from two independent experiments. Again, orogastric gavage with *L. reuteri* 6475 significantly reduced weight loss and colon damage compared with media control group. Mice received hdcA mutant significantly increased weight loss and macroscopic inflammation in the colon compared with mice that received wild type bacteria, showing that hdcA mutant yields diminished ability to attenuate colitis.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of treating and/or reducing the risk of developing an inflammatory disease or condition in a mammal, comprising:
   administering to a mammal in need thereof a lactic acid bacterial strain that produces histamine, wherein the lactic acid bacterial strain comprises an hdcA gene, an hdcB gene and a histidine/histamine antiporter gene, thereby treating and/or reducing the risk of developing an inflammatory disease or condition in the mammal.

2. The method of claim 1, wherein the lactic acid bacterial strain is not *Lactobacillus reuteri* 6475 (ATCC PTA 6475).

3. The method of claim 1, wherein the administration is oral and/or topical and provides local production of histamine.

4. The method of claim 1, wherein the lactic acid bacterial strain is a strain of *Lactobacillus reuteri*.

5. The method of claim 1, wherein the inflammatory disease or condition is in the gastrointestinal tract (GI tract), the genitourinary tract (GU tract), oral cavity, lungs, and/or airways of said mammal, and/or is on the skin of said mammal.

6. The method of claim 1, wherein the inflammatory disease or condition is selected from the group consisting of colitis, inflammatory bowel disease, irritable bowel syndrome, diverticulosis, gingivitis, vaginitis, and any combination thereof.

7. The method of claim 1, further comprising administering at least one further therapeutic and/or nutritional agent to the mammal.

8. The method of claim 7, wherein said further therapeutic or nutritional agent comprises histidine or a histidine analog, an appropriate carbon source which supports the production of histamine by said strain, or a combination thereof.

9. The method of claim 8, wherein the histidine or histidine analog is comprised in a foodstuff or a food supplement.

10. The method of claim 8, wherein the carbon source comprises glucose.

\* \* \* \* \*

UNITED STATES PATENT AND TRADEMARK OFFICE
CERTIFICATE OF CORRECTION

PATENT NO. : 10,898,529 B2
APPLICATION NO. : 15/987210
DATED : January 26, 2021
INVENTOR(S) : Versalovic et al.

It is certified that error appears in the above-identified patent and that said Letters Patent is hereby corrected as shown below:

In the Specification

Column 5, Line 48: Please correct "H4receptor" to read -- $H_4$receptor --

Column 5, Line 61: Please correct "*(INF)*" to read -- *(TNF)* --

Column 8, Line 42: Please correct "colitis. IBD. IBS," to read -- colitis, IBD, IBS, --

Column 15, Line 55: Please correct "B3. B5" to read -- B3, B5 --

Signed and Sealed this
Fourth Day of May, 2021

Drew Hirshfeld
*Performing the Functions and Duties of the
Under Secretary of Commerce for Intellectual Property and
Director of the United States Patent and Trademark Office*